United States Patent
Clopton

(10) Patent No.: US 8,845,099 B2
(45) Date of Patent: Sep. 30, 2014

(54) SYSTEM AND METHOD FOR REAL TIME MONITORING AND DYNAMIC TREATMENT OF OCULOMOTOR CONDITIONS

(71) Applicant: Jason Clopton, Cookeville, TN (US)

(72) Inventor: Jason Clopton, Cookeville, TN (US)

( * ) Notice: Subject to any disclaimer, the term of this patent is extended or adjusted under 35 U.S.C. 154(b) by 101 days.

(21) Appl. No.: 13/627,406

(22) Filed: Sep. 26, 2012

(65) Prior Publication Data

US 2014/0085608 A1    Mar. 27, 2014

(51) Int. Cl.
*A61B 3/14* (2006.01)
*A61B 3/10* (2006.01)
*A61B 3/113* (2006.01)

(52) U.S. Cl.
CPC .. *A61B 3/113* (2013.01); *A61B 3/10* (2013.01)
USPC ............................. 351/209; 351/204; 351/246

(58) Field of Classification Search
CPC ............ A61B 3/10; A61B 3/11; A61B 3/111; A61B 3/113; A61B 3/08; A61B 3/085; A61H 5/00
USPC .................. 351/200–205, 209–210, 211, 246
See application file for complete search history.

(56) References Cited

U.S. PATENT DOCUMENTS

| | | | |
|---|---|---|---|
| 5,094,521 A * | 3/1992 | Jolson et al. .................. | 351/210 |
| 5,293,187 A | 3/1994 | Knapp et al. | |
| 5,530,492 A * | 6/1996 | Ron .............................. | 351/201 |
| 5,550,601 A * | 8/1996 | Donaldson .................... | 351/209 |
| 5,821,989 A | 10/1998 | Lazzaro et al. | |
| 6,511,175 B2 * | 1/2003 | Hay et al. ......................... | 351/45 |
| 7,033,025 B2 | 4/2006 | Winterbotham | |
| 7,699,466 B2 * | 4/2010 | Hayakawa et al. ........... | 351/203 |
| 7,878,652 B2 | 2/2011 | Chen et al. | |
| 7,963,652 B2 | 6/2011 | Vertegaal et al. | |
| 2001/0050754 A1 | 12/2001 | Hay et al. | |
| 2005/0041208 A1 | 2/2005 | Winterbotham | |
| 2006/0087618 A1 * | 4/2006 | Smart et al. .................... | 351/222 |
| 2006/0170864 A1 | 8/2006 | Kuiper et al. | |
| 2008/0062338 A1 | 3/2008 | Herzog et al. | |

(Continued)

FOREIGN PATENT DOCUMENTS

| | | |
|---|---|---|
| JP | 2012-095997 A | 5/2012 |
| WO | 2011021936 | 2/2011 |

OTHER PUBLICATIONS

International Search Report in corresponding International Application PCT/US2013/061899, dated Jan. 13, 2014, 3 pp.

*Primary Examiner* — Thomas K Pham
*Assistant Examiner* — Nicholas Pasko
(74) *Attorney, Agent, or Firm* — Waddey Patterson; Gary L. Montle

(57) ABSTRACT

Systems and methods are provided for monitoring eye movements of a user, and diagnosing and treating eye conditions substantially in real-time. A visual display device is provided with optical display fields corresponding to eyes of the user, and a controller linked to the device is programmed to measure eye positions with respect to the display device and determine optical deviations in any eye with respect to a central visual axis of the other (dominant) eye. In response to deviations exceeding a first value, an occlusion spot is generated in the display field for the dominant eye of a size corresponding to the degree of optical deviation. The location of the occlusion is continuously adjusted in accordance with real-time movements of the dominant eye based on the received signals from the device. When the optical deviation falls below a second value, occlusion of the dominant eye is disabled.

20 Claims, 2 Drawing Sheets

(56) References Cited

U.S. PATENT DOCUMENTS

2009/0005756 A1    1/2009  Foster
2010/0073469 A1*   3/2010  Fateh .............................. 348/62
2010/0110377 A1    5/2010  Maloca et al.
2012/0019779 A1*   1/2012  Legerton et al. .............. 351/209
2012/0307203 A1*   12/2012 Vendel et al. ................. 351/201

* cited by examiner

SYSTEM AND METHOD FOR REAL TIME MONITORING AND DYNAMIC TREATMENT OF OCULOMOTOR CONDITIONS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference: None

BACKGROUND OF THE INVENTION

The present invention relates generally to dynamically diagnosing and treating conditions related to oculomotor functioning in real time. More particularly, the present invention relates to a system and method for tracking movements of the eye in real time and supplying dynamic therapeutic processes to address certain oculomotor conditions as may be determined from the eye tracking diagnoses, such as for example strabismus.

Eye movements are developed through subcortical reflexes with cortical integration based on genetic influences, learned responses, pathologies, and the adaptation process.

Strabismus (eye turn) is defined as a condition where the eyes are not properly aligned with each other. The prevalence of strabismus is reported to be between 2-5 percent of the population of the world with higher prevalence being reported in sub-populations of race, birth weight, and other factors.

Amblyopia, defined as poor vision due to abnormal visual experience early in life, affects approximately 3 percent of the population and carries a lifetime risk of visual loss of at least 1.2 percent. The presence of amblyopia or its risk factors, mainly strabismus or refractive error, have been primary conditions targeted in childhood. Continued support for amblyopia screenings requires evidence-based understanding of the prevalence and natural history of amblyopia and its predisposing conditions, and proof that treatment is effective in the long term with minimal negative impact on the patient and family.

These conditions have traditionally been treated with orthoptics, static therapies (e.g., patching), and vision therapies or surgical repositioning of eye muscles. Surgery is performed in the hopes that the brain would start to integrate the signal from the eye that is turned or otherwise has a lesser degree of functioning. While therapeutic means of treatment has a high functional success rate, it generally takes a great deal of time and effort for the practitioner and the patient. Surgery, on the other hand, has a high rate of cosmetic success but a poor rate of functional success, with side effects, and often requires multiple surgeries on the same patient with lesser functional success.

BRIEF SUMMARY OF THE INVENTION

A system and method are provided in accordance with the present invention for tracking eye movement, and for diagnosing and treating substantially in real-time aspects of the dynamic visual process.

Briefly stated, systems and methods are provided for monitoring eye movements of a user, and diagnosing and treating eye conditions substantially in real-time. A visual display device is provided with optical display fields corresponding to eyes of the user, and a controller linked to the device is programmed to measure eye positions with respect to the display device and determine optical deviations in any eye with respect to a central visual axis of the other (dominant) eye.

In response to deviations exceeding a first value, a primary treatment is initiated wherein an occlusion spot is generated in the display field for the dominant eye of a size corresponding to the degree of deviation of line of sight of the dominant eye. The location of the occlusion is continuously adjusted in accordance with real-time movements of the dominant eye based on the received signals from the device. When the optical deviation falls below a second value, occlusion of the dominant eye is disabled.

Subsequently, in a secondary treatment phase the control unit generates occlusions in the respective display fields for each of said first and second eyes in an alternating fashion, with a first occlusion about the central visual axis of the display field of said second eye, and a second occlusion about a periphery of the display field of said first eye. In various embodiments according to the present invention this may for example be a programmed treatment phase that can be selectively implemented by a physician.

In an aspect of the present invention, the occlusion for the first eye extends to the determined degree of deviation from line of sight of the second (dominant) eye, and the occlusion for the second eye extends from the determined degree of deviation from line of sight of the dominant eye to the periphery of the display field, and the first and second occlusions are alternated at a predetermined frequency.

In another aspect, the alternating occlusions in the secondary treatment phase may have variable timing.

In another aspect, an occlusion is generated in the display field for the second eye when the degree of the determined deviation from line of sight of the dominant eye exceeds a first predetermined threshold value for at least a predetermined period of time.

In another aspect, the visual display device includes a plurality of neutral density filters wherein occlusions may be generated in variable neutral density.

In another aspect, a visual motion stimulation process may be generated in accordance with determination of a nasal/temporal drift condition for the user. The visual motion stimulation process may be an optokinetic nystagmus (OKN) process. The nasal/temporal drift condition may be associated with a deviation of the first eye of five degrees or more from a central visual axis associated with the second eye.

In another aspect, the system may be programmed to monitor eye positions of the user to determine eye movement patterns, compare the determined eye movement patterns with data stored in a database and associated with one or more conditions affecting oculomotor dysfunctions, and generate a predictive report with respect to one or more of said conditions based on a comparison result and a user profile.

In another aspect, each of parasaggital (X), horizontal (Y), vertical (Z), and rotational (R) eye positions for the user may be monitored with respect to time.

DETAILED DESCRIPTION OF THE INVENTION

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

The term "coupled" as used herein means at least either a direct electrical connection between the connected items or an indirect connection through one or more passive or active intermediary devices. The term "circuit" as used herein means at least either a single component or a multiplicity of components, either active and/or passive, that are coupled together to provide a desired function. The term "signal" as used herein may include any meanings as may be understood by those of ordinary skill in the art, including at least an electric or magnetic representation of current, voltage, charge, temperature, data or a state of one or more memory locations as expressed on one or more transmission mediums, and generally capable of being transmitted, received, stored, compared, combined or otherwise manipulated in any equivalent manner.

Exemplary Embodiments

Figure 1:
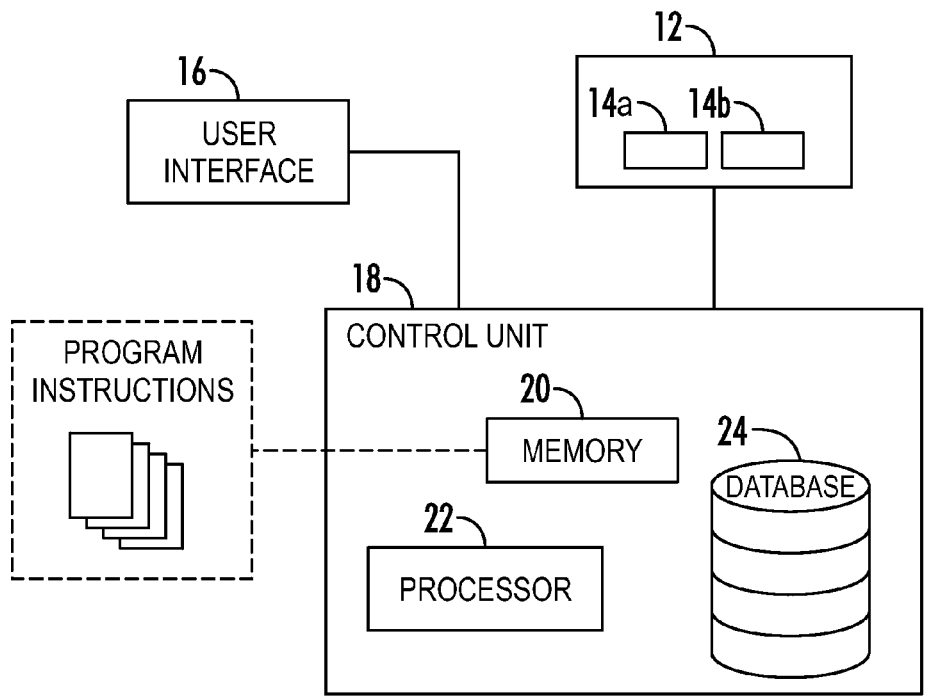
FIG. 1 is a block diagram representing an embodiment of a system according the present invention.
Figure 2:
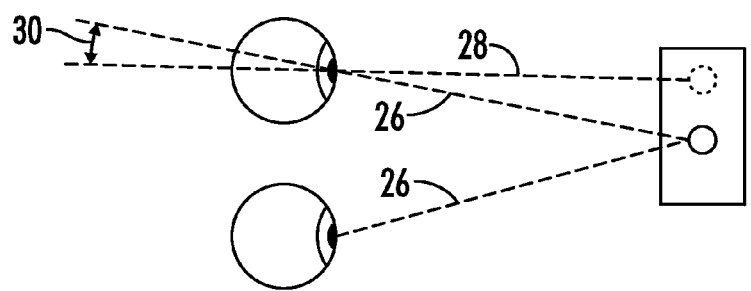
FIG. 2 is a graphical diagram representing an exemplary eye deviation measured by the system of FIG. 1.
Figure 3:
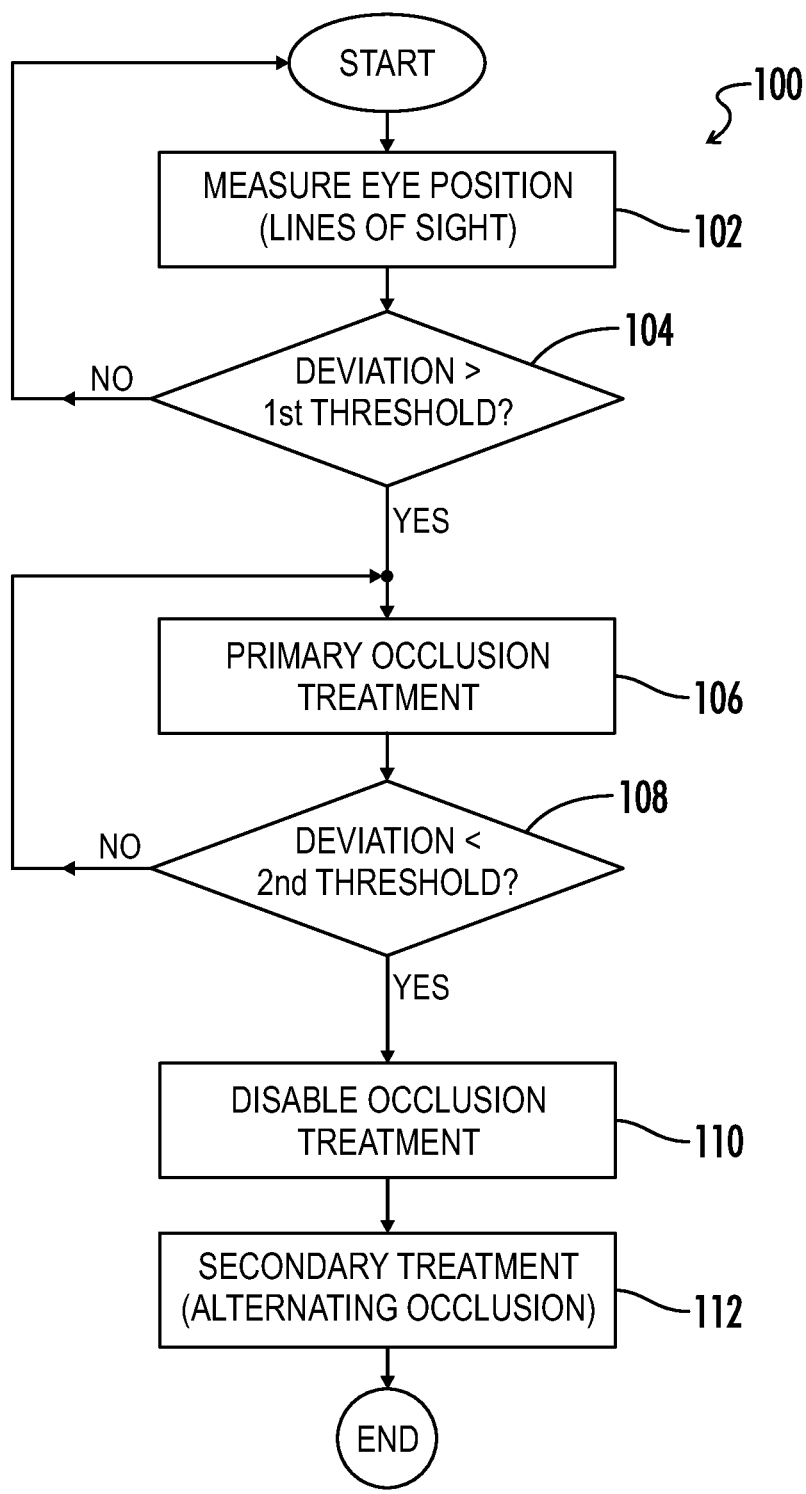
FIG. 3 is a flowchart representing an exemplary method according to the present invention.

Referring generally to FIGS. 1-3, various embodiments of systems and methods according to the present invention may be described herein. Where the various figures may describe embodiments sharing various common elements and features with other embodiments, similar elements and features are given the same reference numerals and redundant description thereof may be omitted below.

More particularly with reference to FIG. 1, an exemplary system 10 of the present invention may include at least a visual display unit 12 for users, a user interface 16 for physicians or other practitioner, and a back-end control unit (controller) 18.

In various embodiments the visual display portion 12 may be a display medium such as for example LCD glasses or an equivalent device having first and second display fields 14a, 14b, respectively, and communicatively linked to a separate and perhaps even a remotely located control unit 18. Alternatively, a single housing may be provided within the scope of the present invention as including or otherwise embodying the various units or modules as described herein.

Referring to FIG. 2, the display medium 12 may include sensors and programming effective to determine deviations 30 in the line of sight of a first eye 26 with respect to the line of sight of a second eye 28, and generate output signals representative of the determined deviations 30, among other functions. Alternatively, the display medium may be configured within the scope of the present invention to provide raw output signals representative of the detected eye positions, with the controller programmed to determine eye movements, deviations, and other data as needed to perform the functions further described herein.

The control unit 18 may generally include one or more non-transitory computer-readable media 20 and a processor 22. The term "computer-readable memory medium" 20 as used herein may refer to any non-transitory medium alone or as one of a plurality of non-transitory memory media within which is embodied a computer program product that includes processor-executable software, instructions, program modules, etc., which upon execution may provide data or otherwise cause a computer system to implement subject matter or otherwise operate in a specific manner as further defined herein. It may further be understood that more than one type of memory media may be used in combination to conduct processor-executable software, instructions or program modules from a first memory medium upon which the software, instructions or program modules initially reside to a processor for execution. The media may further include storage media 24 upon which reside, e.g., databases such as for example transaction or operational databases, informational databases, data warehouses, data marts, etc., as effective to store data for various functions as recited herein and in various manners as may be understood by those of skill in the art.

The term "user interface" as used herein may unless otherwise stated include any input-output module communicatively linked to the control unit including but not limited to LCD displays, web portals, such as individual web pages or those collectively defining a hosted website, mobile desktop applications, telephony interfaces such as interactive voice response (IVR), and the like. Such interfaces may in a broader sense include pop-ups or links to third party websites for the purpose of further accessing and/or integrating associated materials, data or program functions via the hosted system and in accordance with methods of the present invention.

Briefly stated, an embodiment of a system 10 according to the present invention may generally be configured to monitor and treat basic eye movement functioning deficits through, e.g., variable size sectoral and/or central occlusion, including expandable/contractible central/peripheral full spectrum occlusion. The occlusion may typically follow the eye as needed.

Referring now to FIG. 3, an exemplary method 100 according to the present invention begins with the measurement of positions for each of a first and second eye associated with a user (step 102). In certain embodiments, as alluded to above, the display medium may process the eye position (line of sight) data and generate output signals representative of an eye deviation between the first and second eye positions (lines of sight). In other embodiments, the display medium may merely transmit raw data signals corresponding to the eye positions, wherein the processing of the data to determine a first (visual) line of sight (with respect to a dominant eye) and deviations of a second line of sight (in the non-dominant eye and with respect to the visual line of sight) is performed in the control unit. The measurement of eye positions via such a display medium is itself well known in the art and further description of the same may be omitted here, as any of a number of different methods may be utilized within the scope of the present invention.

During the diagnostic phase, it may typically be desirable that the provider should gather as much eye movement data for individual patients for a set period of time having the patient go about their daily routine with emphasis on true distance viewing in an outdoor environment and true near point viewing in an outdoor and indoor environment including computers, reading, crawling or other near point tasks. Maximal vestibular input may be encouraged as the patient's day to day routines include a great deal of vestibular stimulation for normal activities.

The method continues by determining whether or not an eye deviation condition is present based on the most recent set of eye position measurements (step 104). An eye deviation condition as referred to herein may be defined as a deviation from a central visual axis of greater than a predetermined value (e.g., 2 degrees) with respect to that of the dominant eye. In various embodiments, when the deviating eye turns more than the predetermined amount (e.g., 2 degrees) from the visual axis of the dominant eye for more than a predetermined amount of time (e.g., 500 ms) treatment may be initiated by the control unit.

In cases of amblyopia/micro-strabismus, anomalous retinal correspondence, etc., wherein an eye treatment condition has been initiated by the control unit, a primary response may be to generate an occlusion spot with respect to the central visual axis of the non-deviating eye (step 106), a size of the occlusion spot generally matching the size of the deviation from binocular of the other eye. The occlusion may typically be generated by the display medium in accordance with control signals received from the control unit, wherein what previously had been a substantially transparent display field with respect to each of the first and second eyes of the user is now blocked at least in part with respect to the dominant (i.e., non-deviating) eye. The occlusion spot may typically be round in shape, but various alternative configurations may be provided in accordance with predetermined criteria such as physician input.

In an embodiment, the size of the occlusion spot can be determined by the amount of the measured deviation of the deviating eye. A full spectrum occlusion spot is generated two degrees more than the actual deviation (i.e., a strabismus turning to 20 diopters would have a spot occlusion on the dominant eye of 2 degrees more than 20 diopters)

Alternatively, the size of the occlusion spot may be predetermined in accordance with criteria such as, e.g., at the discretion of the eye care physician.

When the deviating eye returns to within a second predetermined threshold value (e.g., 1 degree of alignment of the visual axis of the dominant eye), the primary occlusion treatment may generally be disabled by the control unit (steps 108,110).

When the primary response is resolved and the deviating eye has substantially achieved alignment, the control unit may implement a secondary treatment response (step 112). In an embodiment, a full spectrum occlusion may be generated about the central visual axis of the non-deviating eye up to the size of the previously deviating eye angle, and a full spectrum occlusion may further be generated about the periphery of the deviating eye from the size of the deviation to the outer perimeter of the LCD. The full spectrum occlusion of the secondary treatment phase may generally be alternated back and forth with respect to the deviating and non-deviating eyes at a predetermined frequency (e.g., 65 Hz) or otherwise at a rate programmable by the physician. The size of the central/peripheral occlusions may be configured to match the size of the deviating eye down to for example twenty seconds of arc or any desired combination of central and peripheral occlusion and alternating frequency to be determined by the practitioner. In an embodiment, further user entry parameters and associated control algorithms may be available such that these functions may also be variably controlled by the physician as desired.

In an embodiment within the scope of the present invention, the control unit may implement variable or static nasal/temporal occlusion based on eye positioning as or otherwise within the primary treatment phase. When the non-dominant eye drifts into the nasal/temporal field so as to define a nasal/temporal drift condition for the user (especially in cases of infantile strabismus or abduction deficits and cross fixation patterns), the bi/uni nasal or temporal occlusion will be enabled with varying size based on positioning of the eye (i.e., as the non-dominant eye starts to turn, an occlusion spot is generated for the dominant eye to the size of the turn of the deviating eye from the visual axis). In some cases, the presence of a nasal/temporal drift condition may be absolutely defined with respect to a deviation greater than a threshold value from the central visual axis of a dominant eye. In other cases, the presence of a nasal/temporal drift condition so as to trigger the occlusion described herein may only be determined with further respect to characteristics of the particular user (e.g., a child, elderly, a user with previously diagnosed conditions, etc.).

The physician may be enabled to choose if they want the bi- or uni-nasal occlusion set at the limbus or any other position relative to the limbus of the eye (e.g, one degree nasal of limbus or two degrees temporal of limbus, or the like) rather than for example positioning the occlusion strictly with respect to the central visual axis as previously described.

In various embodiments, the control unit may further implement or otherwise direct the performance of optokinetic nystagmus (OKN)/visual motion processing stimulation with respect to the first and second display fields from nasal to temporal or temporal to nasal, e.g., at an approximate speed of 2 Hz. When the non-dominant eye drifts into the nasal/temporal field or otherwise triggers a nasal/temporal drift condition as described above, the OKN stimulation process may engage until the drifting eye is aligned to the positioning of the dominant eye or until one of the occlusive processes brings the non-dominant eye back to alignment. This process may be accompanied by one or more of the other occlusive/stimulation functions as desired.

Once alignment has been substantially achieved, all occlusion/stimulation processes may typically be discontinued and re-established as needed in real time, such as when an eye alignment drift is detected or as determined by the physician.

In an embodiment, the system may be configured to monitor and treat basic and non-basic eye movement functioning deficits. An LCD matrix technology may be utilized including, e.g., variable neutral density filters wherein occlusion spots generated by the control unit may be variable in neutral density.

In an embodiment, the occlusion spots generated by the control unit during, e.g., the secondary treatment phase may further be variable with respect to the timing of on/off steady states.

Systems according to the present invention may be configured to provide basic information for the diagnosis and treatment of basic and non-basic eye movement functioning deficits. One or more local databases may define a library of eye movement functionality to draw from for diagnostic purposes, or otherwise the system may rely on various remote databases as needed to perform the diagnostic and predictive functions described herein.

In an embodiment, the display medium may be configured such that it is able to be placed on a patient of any age and left on for a period of time that will allow for the device to monitor eye movements and potentially draw from a database of normative/abnormal movements to be able to recommend a potential diagnosis of conditions that affect eye movement dysfunction (e.g., brain injury, concussions, vestibular dysfunction, strabismus, amblyopia, oculomotor dysfunction and the like). While in various embodiments of the present invention, only a limited range of eye movement detection may be required to perform certain functions as described herein, it may be considered for optimal monitoring of eye movements that the device will measure X (parasaggital), Z (vertical), Y (transverse/horizontal), and R (rotational) positioning with respect to time.

Embodiments of the system so configured may be able to monitor, provide basic and higher level information for the diagnosis and treatment of basic and non-basic movement functioning deficits as well as predictive eye movements based on prior database collected information and current user information. Using this information, the system may execute various additional algorithms to provide a predictive function and be able to predict potential difficulties from younger ages to the future and function as a remediation for such possible conditions.

Examples may include oculomotor dysfunctions in infants, patterns of eye movements for schizophrenia, Alzheimer's, mTBI, ADD/ADHD, near point task movement difficulties and other diagnosis. Balance and fall risk predictions may be assessed on the elderly and those with potential balance dysfunction. Eye movement effects of concussion may be available for diagnosing concussions at the time of the incident.

In an embodiment, the system may further include one or more sensors for gravitational positioning and head acceleration/deceleration monitoring. The control unit in such an embodiment is programmed to incorporate vestibular sensing with ocular function and therefore incorporates horizontal, vertical and tilt functions into the treatment abilities.

With respect to the various embodiments of a system of the present invention as described above, an exemplary treatment protocol programming may take into consideration the Vestibulo-ocular reflex (VOR) (16 msec) as the core of all eye movements. While there are many, many other sensory inputs to eye movement functioning, this is the primary reflex involved.

The control unit (or alternatively the display medium itself where the programming is decentralized as with certain embodiments described herein) may be programmed to monitor a number of basic eye movements including but not limited to those described herein, and further without express limitation as to parameters provided. The vestibulo-ocular reflex (VOR) may be measured with 16 msec latency. The control unit may further measure pursuits with 90-150 msec latency—i.e., smooth movement of the eyes tracking an object(s) of regard from point A to point B without a jump and corresponding loss or blur of central acuity and the object(s) of regard. The control unit may further measure saccades with 150-250 msec latency—i.e., a fast jump from point A to point B with a loss of central acuity and no blur from A to B, decreasing central acuity so that the patient moving their eyes does not have blur, diplopia, and confusion while the eyes are moving from A to B. These movements may each be mediated with the VOR and OKN.

Diagnostic Mode and Calibration

In various embodiments the user interface for physicians may be configured so as to enable central occlusion programming, the generation of patient profiles, etc. Typically, the programming may enable the user (eye care or other physician) to enter patients' date of birth, pupillary distance with central fixation of dominant and non-dominant eye, angle and approximate degrees of deviation of the non-dominant eye and angle of eccentric fixation, anomalous retinal correspondence, or micro-strabismus, etc. These data entries may, e.g., guide the program as to the initial recommended size of the central fixation occlusion spot, even though as described above the central occlusion spot may desirably be variable in order to get larger or smaller depending on the amount of non-dominant eye turn measured.

During an exemplary diagnostic mode, the system will start with the patient's current refractive compensation and monitor eye movements until the database has enough information to determine dominant eye, angle of deviation and time of deviation. The provider will input the following information into the primary screen: first name, middle initial, last name, date of birth, sex, patient number is assigned, and currently used spectacle refractive status including prism (ground in or decentered), and best compensated acuity with currently used spectacles. Once this information is put in, the practitioner may choose to put secondary information in the database like tentative diagnosis or other patient-specific information.

The patient will then be encouraged to look at a distance target with each eye to determine stability of gaze with each eye (occluding the left eye, allowing the device to gather distance viewing gaze data, then occluding the right eye and allowing the device to gather distance viewing gaze data), then encourage the patient to look at a near target to determine stability of near viewing gaze data in the same sequence of the distance viewing sequence.

After gathering the distance and near gaze data, the patient may then be run through extraocular motility (EOM) testing in a slow circular tracking motion.

Calibration points may typically be delineated, examples of which may be as further described herein. There may be five points on the initial screen that the doctor should pick as the tracking areas (similar to OCT picking of the ONH). The most difficult points are typically the bottom corners due to angles and lowering of the eyelids. Corneal deforming and iris deforming can be provided as measures of angle from straight ahead. For the dominant eye, dominance may be used as the measure of straight as determined by the eye care provider. For binocular calibration, separate calibration of each eye is needed. These will be compared and recalculated as needed by the device. For corneal shape, the system may be integrated with corneal topography with an area in the user interface for the eye care provider to automatically pull data in or manually input, to account for corneal shapes that may be different enough to affect outcomes of measurement (e.g., lasik patients, keratoconus, corneal transplant, high astigmatism, myopia, hyperopia, etc.). For refractive condition, the system may integrate with refractive state of the patient to allow for spectacle compensation to be accounted for having better accuracy on tracking.

If further specific testing such as DVA (dynamic visual acuity), gaze evoked nystagmus, video oculography, or video nystagmography are required, in various embodiments a dropdown menu for this may be provided in the user interface.

Determining Oculomotor Events of Interest

It may generally be considered that the input of raw data does not always correlate with the output of information, and therefore various embodiments of a system according to the present invention may include various parameters and algorithms for determining oculomotor events of interest (EOI) from the raw data EOI calculation may be derived in accordance with parameters including but not limited to, e.g., gaze position (x,y); gaze velocity (in o/s); gaze acceleration (in o/s2); pupil size; blink and (determined by x=0, y=0, and pupil diameter of 0)

Scan Paths describe how the eye physically moves through space, typically but not exclusively for one patient or the route of oculomotor events through space within a certain timespan.

Normal eye movements may be defined as those that are defined above that do not interfere with binocularity and enhance functioning of the patient in their activities of daily living.

Abnormal eye movements may be defined as those that are defined above with the two eyes deviating to the point of interference of activities of daily living. These would be eye movements that act to decrease or limit binocularity or functionality of vision.

When a convergence movement is made, both eyes are converging to the object of regard. This can be in a pathway straight ahead on the midline of the patient or at any angle from straight ahead. This means that the eyes are both moving in a movement that follows the object of regard. This must be differentiated from a strabismic movement where the strabismic eye deviates from the object of regard in a movement that is different from the dominant eye. This will include a saccade away from the smooth pursuit of the dominant in a tropic posture.

The eyes have small short conjugate and disconjugate eye movements at all times. There are normal, slight disconjugate eye movements always present in any eye movements, even in conjugate movements like saccades, and in pursuits there are small disconjugate movements that are controlled by the VOR response. These small movements may be the key to differentiating object positions for stereopsis cues. These should be measured and recorded for amount and time.

The previous detailed description has been provided for the purposes of illustration and description. Thus, although there have been described particular embodiments of the present invention of a new and useful "System and Method of Real Time Monitoring and Dynamic Treatment of Oculomotor Conditions," it is not intended that such references be construed as limitations upon the scope of this invention except as set forth in the following claims.

What is claimed is:

1. A system for real-time diagnosis and treatment of optical conditions, the system comprising:
    a visual display device effective in response to input display signals to generate first and second optical display fields corresponding to first and second eyes of a user of the device, the device further comprising one or more sensors effective in combination to detect optical data for each eye associated with the user and to generate corresponding output signals;
    a controller communicatively coupled to receive the output signals from the device and further comprising a processor and a non-transitory computer-readable medium having program instructions stored therein, the instructions executable by the processor to cause the controller to perform steps comprising
        (a) determining an optical deviation in a first eye of the user with respect to a central visual axis associated with a second eye,
        (b) comparing the determined optical deviation to a first predetermined threshold value,
        (c) when the degree of the determined optical deviation exceeds the first predetermined threshold value, providing display signals to the display device for generating an occlusion spot in the display field for the second eye, the occlusion spot having a size corresponding to the determined degree of optical deviation,
        (d) adjusting the location of the occlusion in accordance with real-time movements of the second eye based on the received signals from the device, and
        (e) when the degree of the determined optical deviation falls below a second predetermined threshold value, disabling the occlusion in the display field of the second eye.

2. The system of claim 1, steps (a) to (e) defining a primary treatment response, the instructions further executable by the processor upon disabling the occlusion to cause the controller to perform a second treatment response comprising steps of
    (f) alternately generating occlusions in the respective display fields for each of said first and second eyes.

3. The system of claim 2, wherein step (f) further comprises alternately generating an occlusion about the central visual axis of the display field of said second eye, and an occlusion about a periphery of the display field of said first eye.

4. The system of claim 3, the alternately generated occlusion for the first eye extending to the determined degree of optical deviation of the second eye, the alternately generated occlusion for the second eye extending from the determined degree of optical deviation to the periphery of the display field.

5. The system of claim 2, wherein the step of alternately generating occlusions in the respective display fields for each of said first and second eyes further comprises alternately generating occlusions having variable timing with respect to the off/on steady states for each of said first and second eyes.

6. The system of claim 1, step (c) further comprises generating an occlusion in the display field for the second eye when the degree of the determined deviation exceeds a first predetermined threshold value for at least a predetermined period of time.

7. The system of claim 1, the visual display device comprising a plurality of neutral density filters, the instructions further executable by the processor to cause the controller to generate variable occlusions in neutral density.

8. A system for real-time diagnosis and treatment of optical conditions, the system comprising a user display medium having first and second visual display fields communicatively linked to a non-transitory computer-readable medium having program instructions stored therein, the instructions executable by a processor to direct the performance of a method comprising the steps of:
    measuring positions for first and second eyes of a user;
    determining a position of the first eye of the user as corresponding to a nasal/temporal drift condition;
    generating an occlusion in the display field for the second eye, the occlusion having a size corresponding to the determined degree of deviation and located with respect to the measured position of the second eye;
    adjusting the location of the occlusion in accordance with real-time movements of the second eye; and
    when the degree of the determined optical deviation falls below a second predetermined threshold value, disabling the occlusion in the display field of the second eye.

9. The system of claim 8, the instructions executable by a processor to direct the performance of a visual motion stimulation process in accordance with determination of said nasal/temporal drift condition.

10. The system of claim 9, the visual motion stimulation process comprising an optokinetic nystagmus (OKN) process.

11. The system of claim 10, the nasal/temporal drift condition associated with a deviation of the first eye of five degrees or more from a central visual axis associated with the second eye.

12. The system of claim 8, the instructions executable by a processor to direct the performance of steps further comprising:
   monitoring eye positions of the user to determine eye movement patterns;
   comparing the determined eye movement patterns with data stored in a database and associated with one or more conditions affecting eye movement dysfunctions; and
   generating a predictive report with respect to one or more of said conditions based on a comparison result and a user profile.

13. The system of claim 12, the step of monitoring eye positions of the user to determine eye movement patterns comprising measuring each of parasaggital (X), horizontal (Y), vertical (Z), and rotational (R) eye positions with respect to time.

14. A method of real-time diagnosis and treatment of optical conditions, the method comprising:
   measuring positions for first and second eyes of a user looking through first and second LCD display fields, respectively;
   determining an optical deviation in the first eye position with respect to a central visual axis associated with the second eye;
   when a degree of the determined optical deviation exceeds a first predetermined threshold value, generating an occlusion spot in the second display field, the occlusion spot having a size corresponding to the determined degree of optical deviation;
   continuously adjusting the location of the occlusion in accordance with real-time movements of the second eye; and
   when the degree of the determined optical deviation falls below a second predetermined threshold value, disabling the occlusion in the second display field.

15. The method of claim 14, further comprising a step upon disabling the occlusion of alternately generating occlusions in the respective display fields for each of said first and second eyes.

16. The method of claim 15, the step of alternately generating occlusions in the respective display fields for each of said first and second eyes further comprising alternately generating occlusions about the central visual axis of the display field of said second eye, and an occlusion about a periphery of the display field of said first eye.

17. The method of claim 16, the alternately generated occlusion for the first eye extending to the determined degree of optical deviation of the second eye, the alternately generated occlusion for the second eye extending from the determined degree of optical deviation to the periphery of the display field.

18. The method of claim 15, wherein the step of alternately generating occlusions in the respective display fields for each of said first and second eyes further comprises alternately generating occlusions having variable timing with respect to the off/on steady states for each of said first and second eyes.

19. The method of claim 14, wherein the step of generating an occlusion in the display field for the second eye when a degree of the determined deviation in the first eye exceeds a first predetermined threshold value further comprises generating an occlusion in the display field for the second eye when the degree of the determined deviation in the first eye exceeds a first predetermined threshold value for at least a predetermined period of time.

20. The method of claim 14, further comprising:
   monitoring parasaggital (X), horizontal (Y), vertical (Z), and rotational (R) eye positions of the user with respect to time to determine eye movement patterns;
   comparing the determined eye movement patterns with data stored in a database and associated with one or more conditions affecting eye movement dysfunctions; and
   generating a predictive report with respect to one or more of said conditions based on a comparison result and a user profile.

* * * * *